United States Patent [19]

Chen

[11] Patent Number: 5,397,574
[45] Date of Patent: Mar. 14, 1995

[54] CONTROLLED RELEASE POTASSIUM DOSAGE FORM

[75] Inventor: Chih-Ming Chen, Cooper City, Fla.

[73] Assignee: Andrx Pharmaceuticals, Inc., Fort Lauderdale, Fla.

[21] Appl. No.: 131,118

[22] Filed: Oct. 4, 1993

[51] Int. Cl.[6] .................................................. A61K 9/62
[52] U.S. Cl. ................................... 424/451; 424/457; 424/458; 424/462; 424/463; 424/456
[58] Field of Search ............... 424/461, 456, 462, 451, 424/472, 489, 480

[56] References Cited

U.S. PATENT DOCUMENTS

| | | | |
|---|---|---|---|
| 4,798,724 | 1/1989 | Khanna | 424/480 |
| 4,863,743 | 9/1989 | Hsiao | 424/476 |
| 4,946,685 | 8/1990 | Edgren et al. | 424/472 |
| 5,035,898 | 7/1991 | Chang | 424/474 |
| 5,200,195 | 4/1993 | Dong et al. | 424/473 |
| 5,260,069 | 11/1993 | Chen | 424/489 |

OTHER PUBLICATIONS

Baum et al. Total Body Exchangeable Potassium . . . American Heart Journal 58(2) Jul. 1959 (53–58).

*Primary Examiner*—Thurman K. Page
*Assistant Examiner*—William E. Benston, Jr.
*Attorney, Agent, or Firm*—Alvin S. Blum

[57] ABSTRACT

A pharmaceutical composition for oral administration of potassium salt in a form not irritating to the gastrointestinal mucosa comprises tablets or capsules of micropellets of a potassium salt, such as potassium chloride. The micropellets are coated with a permeable polymer comprising a low viscosity (10 cp.) ethylcellulose in combination with triacetin. This coating provides a strong film resistant to breakage during formation of tablets and filling of capsules. The protective coating of the micropellets prevents the early release of potassium ions, while the tablet or capsule disintegrates and the micropellets are dispersed within the lumen of the gastrointestinal tract. As water passes through the permeable but insoluble coating, potassium ions are gradually eluted into the fluid of the tract over a period of many hours, thereby allowing time for the ions to be absorbed from the tract before high, irritating ion concentrations can form.

18 Claims, No Drawings

CONTROLLED RELEASE POTASSIUM DOSAGE FORM

BACKGROUND OF THE INVENTION

This invention relates to oral administration forms of potassium, and more particularly to controlled release tablets or capsules containing potassium chloride in a form which releases the drug gradually over a prolonged period of time after ingestion to protect the gastrointestinal tract from the irritation and toxicity accompanying high potassium ion concentrations.

Potassium is the principal intracellular cation in mammals. It is present in a concentration of approximately 140 meg/L inside the cell. The intracellular potassium may be lost over a period of time from various stressful and debilitating conditions including diuretic drug treatment. As the intracellular potassium is depleted, various cells, including heart muscle, become dysfunctional, eventually resulting in death. Various means are available for correcting potassium loss, including direct intravenous injection and oral dosage forms.

Ironically, the potassium ion is quite toxic outside the cell. It normally has a concentration of about five meg/L in extracellular fluids. Levels that are much greater stop cell function. If the required therapeutic dose is injected in concentrated form intravenously, it may kill the patient instantly. When it is administered orally as the potassium chloride salt, it may cause irritation, inflammation and erosion of the mucosal lining of the gastrointestinal tract.

A variety of oral dosage forms of potassium have been developed to provide long term potassium supplements that are less harmful to the user.

U.S. Pat. No. 4,863,743 issued Oct. 5, 1989 to Hsiao provides a review of the prior art of oral therapeutic potassium supplements and the problems they present. He discloses a controlled release tablet formed from potassium chloride crystals coated with a coating mixture of ethylcellulose and one member selected from hydroxypropylcellulose and polyethylene glycol and compressed into tablets with microcrystalline cellulose and crosslinked polyvinylpyrrolidone. He found that low viscosity ethylcellulose was not suitable because the particles broke up during compression. He therefor recommended the high viscosity material of 100 cp., and claims are limited to greater than 40 cp.

U.S. Pat. No. 5,035,898 issued Jul. 30, 1991 to Chang et al. discloses potassium chloride crystals coated with a combination of high viscosity ethylcellulose and at least one of hydroxypropylcellulose and polyethyleneglycol as taught by Hsiao along with a magnesium salt.

SUMMARY OF THE INVENTION

The present invention is an oral dosage form of potassium chloride comprised of potassium chloride crystals coated with a coating comprised of a low viscosity ethylcellulose in combination with triacetin. Applicant has discovered that low viscosity ethylcellulose (10 cp.) when mixed with triacetin makes a coating which does not break when compressed into tablets. This is opposite to the teaching of Hsiao who had to use high viscosity (greater than 40 cp.) ethylcellulose in combination with his other ingredients to reduce breakage on compression.

If any of the coated crystals break with their coating, then the drug is immediately in contact with the mucosa in crystal form, which is extremely irritating.

It is accordingly an object of the invention to provide drug crystals having a non-frangible coating so that the mucosa will be exposed initially to crystals with intact coating. The coating should be such that it is permeable to water and dissolved salt, thereby gradually releasing the drug after the tablet or capsule has dissolved and the individual coated crystals have dispersed.

An advantage of Applicant's coating formulation is that it is more efficient in coating by the fluidized bed coating process because the coating solution may be used at a higher concentration than the high viscosity materials of the prior art, as well as providing a stronger coating. The coated crystals or pellets may be compressed into tablets or introduced into gelatin capsules.

Another object of the present invention is to provide a safe method of treating patients suffering from potassium depletion.

These and other objects, advantages and features will become apparent to those skilled in the art upon further study of the detailed description.

DETAILED DESCRIPTION OF PREFERRED EMBODIMENTS

Micropellets having potassium chloride cores and a water permeable but insoluble coating are first prepared.

The cores are prepared by passing crystalline potassium chloride through a sieve.

The coating solution is prepared by first dissolving ethylcellulose 10 cp. in alcohol and then dissolving triacetin in the solution.

The cores are then coated by spray coating with the solution in a fluidized bed coater and then dried in the coater to form micropellets with a non-frangible coating suitable for tabletting with appropriate tabletting agents without having the coatings fracture from the pressures associated with the tabletting process.

Because the ethylcellulose is of such a low viscosity, the coating solution may be made up in a much higher concentration for faster and more economical coating.

The plasticizer triacetin has been found to enable use of this low viscosity ethylcellulose while reducing frangibility of the resultant coating.

The finished coated micropellets are then ready for incorporation in capsules such as gelatin capsules by well known capsule filling techniques. The finished coated micropellets are then also ready for forming into tablets in combination with tabletting agents well known in the art such as microcrystalline cellulose, cross linked polyvinylpyrrolidone and myvatex to produce a tablet which readily dissolves in an aqueous environment to release the micropellets. The pellets are readily dispersed throughout the gut by the normal peristaltic activity. The individual pellets are permeable to water which passes through the coating to slowly dissolve the potassium chloride core. The dissolved salt passes out through the coating to the gastrointestinal fluid. The elution process is very slow. Because of the delayed release of the salt and the dispersal of the pellets, there are no areas within the gut mucosa subjected to a high concentration of the dissolved potassium. This eliminates the problems associated in the past with potassium supplements which caused irritation and even erosion of the gastrointestinal mucosa.

The following example describes a typical formulation of the coated micropellets, and methods of manufacture thereof:

EXAMPLE I

| | |
|---|---|
| Ethylcellulose, USP 10 cp. dissolved in alcohol SD-3A to a final concentration of | 10% |
| add triacetin USP slowly while stirring to a final concentration of | 2.14% |
| pass potassium chloride crystals USP through a 25 mesh screen. In a fluidized bed coater, coat crystals with the coating solution to a final composition of (weight percent) | |
| potassium chloride | 83% |
| triacetin | 3% |
| ethylcellulose | 14% |
| Dry in coater for five minutes after coating. Prepare tablets from the above coated crystals as follows in a conventional tabletting machine | |

| | Weight % | Mg/tablet |
|---|---|---|
| coated pellets | 93 | 911.4 |
| microcrystalline cellulose | 3 | 29.4 |
| cross linked polyvinylpyrrolidone | 3 | 29.4 |
| myvatex | 1 | 9.8 |

Dissolution Data by constant stirring in water (cumulative % potassium chloride released)

| | 1 hr | 2 hr | 3 hr | 4 hr | 6 hr | 8 hr |
|---|---|---|---|---|---|---|
| coated micropellets | 6 | 24 | 41 | 58 | 86 | 95 |
| tablets | 9 | 27 | 44 | 57 | 85 | 95 |

The above dissolution data is presented as evidence that the coating of the pellets is so strong that the conversion into tablets has not caused any substantial early release of the salt such as would be harmful to the user.

The triacetin serves as a plasticizer in the coating which makes it more resistant to breakage. Other plasticizers which may be used for this purpose include: propylene glycol; triethyl citrate; tributyl citrate; and diethylphthalate. The coating may contain between 70–90% ethylcellulose.

The ethylcellulose may have a viscosity of less than 15 cp.

The potassium chloride is preferably between 20–50 mesh size.

The above disclosed invention has a number of particular features which should preferably be employed in combination although each is useful separately without departure, from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A pharmaceutical dosage unit in tablet form for oral administration of potassium, comprising: a plurality of micropellets having cores of a soluble potassium salt;
   each micropellet being coated with a water insoluble coating comprising
   ethylcellulose and at least one plasticizer, said ethylcellulose having a viscosity of less than 15 cp., and
   comprising between about 70% and 90% by weight of said coating;
   and
   said plurality of micropellets being compressed into tablet form.

2. The dosage unit according to claim 1, in which said cores have a mesh size in the range of from about 20 mesh to 50 mesh.

3. The dosage unit according to claim 2, in which said micropellets, when coated, are comprised of from about 75% to about 90% by weight of potassium chloride.

4. The dosage unit according to claim 3, in which said tablets comprise said micropellets; microcrystalline cellulose; crosslinked polyvinylpyrrolidone and a lubricant and binder.

5. The dosage unit according to claim 4, in which said ethylcellulose has a viscosity of about 10 cp.

6. The dosage unit according to claim 1, in which said plasticizer is triacetin.

7. The dosage unit according to claim 1, in which said at least one plasticizer is selected from propylene glycol, triethyl citrate, tributylcitrate, triacetin and diethylphthalate.

8. A pharmaceutical dosage unit in capsule form for oral administration of potassium, comprising:
   a capsule;
   a plurality of micropellets within said capsule, said micropellets having cores of a soluble potassium salt; and
   each micropellet being coated with a water insoluble coating composition
   comprising ethylcellulose and at least one plasticizer, said
   ethylcellulose having a viscosity of less than 15 cp, and
   comprising between about 70% and 90% by weight of said coating.

9. The dosage unit according to claim 8, in which said cores have a mesh size in the range of from about 20 mesh to 50 mesh.

10. The dosage unit according to claim 9, in which said micropellets, when coated, are comprised of from 75% to 90% by weight of potassium chloride.

11. The dosage unit according to claim 10, in which said ethylcellulose has a viscosity of about 10 cp.

12. The dosage unit according to claim 8, in which said plasticizer is triacetin.

13. The dosage unit according to claim 8, in which said at least one plasticizer is selected from propylene glycol, triethyl citrate, tributyl citrate, triacetin, and diethylphthalate.

14. A pharmaceutical dosage unit in tablet form for oral administration of potassium, comprising:
   a plurality of coated micropellets having cores of potassium chloride;
   a water insoluble coating enclosing each of said cores, said
   coating comprising ethylcellulose having a viscosity of less
   than about 15 cp., and triacetin;
   said plurality of coated micropellets being compressed into
   tablet form in combination with water soluble tabletting agents.

15. The dosage unit according to claim 14, in which said ethylcellulose has a viscosity of about 10 cp.

16. The dosage unit according to claim 15, in which said coated micropellets have a weight composition of about 75%–90% potassium chloride; about 2%–4% triacetin; and about 10%–18% ethyl cellulose.

17. The dosage unit according to claim 16, in which said tabletting agents comprise microcrystalline cellulose, cross linked polyvinylpyrrolidone and a lubricant.

18. The dosage unit according to claim 17, in which said lubricant is myvatex.

* * * * *